United States Patent [19]

Teirstein

[11] Patent Number: 5,468,225
[45] Date of Patent: * Nov. 21, 1995

[54] RAPID EXCHANGE CATHETER

[76] Inventor: Paul S. Teirstein, 402 Coast Blvd., South, La Jolla, Calif. 92037

[*] Notice: The portion of the term of this patent subsequent to Aug. 9, 2011, has been disclaimed.

[21] Appl. No.: 197,970

[22] Filed: Feb. 17, 1994

Related U.S. Application Data

[63] Continuation of Ser. No. 92,332, Jul. 15, 1993, Pat. No. 5,336,184.

[51] Int. Cl.⁶ .................. A61M 29/00; A61M 31/00
[52] U.S. Cl. .................. 604/102; 606/194; 604/53
[58] Field of Search ........... 604/96–103; 606/192–194; 128/656–658

[56] References Cited

U.S. PATENT DOCUMENTS

| 4,762,129 | 8/1988 | Bonzel . | |
| 4,771,777 | 9/1988 | Horzewski et al. . | |
| 4,819,751 | 4/1989 | Shimada et al. . | |
| 4,909,781 | 3/1990 | Husted . | |
| 4,994,745 | 7/1990 | Sogard et al. . | |
| 5,040,548 | 8/1991 | Yock . | |
| 5,061,273 | 10/1991 | Yock . | |
| 5,135,535 | 8/1992 | Kramer . | |
| 5,147,377 | 9/1992 | Sahota . | |
| 5,154,725 | 10/1992 | Leopold . | |
| 5,156,594 | 10/1992 | Keith . | |
| 5,171,222 | 12/1992 | Euteneuer et al. . | |
| 5,180,367 | 1/1993 | Kontos et al. . | |
| 5,205,822 | 4/1993 | Johnson et al. . | |
| 5,232,445 | 8/1993 | Bonzel . | |
| 5,324,269 | 6/1994 | Miraki | 604/96 |
| 5,368,567 | 11/1994 | Lee | 604/102 |

FOREIGN PATENT DOCUMENTS

WO92/17236  10/1992  WIPO .

Primary Examiner—C. Fred Rosenbaum
Assistant Examiner—Frank Wilkens, III
Attorney, Agent, or Firm—Nydegger & Associates

[57] ABSTRACT

An over-the-wire rapid-exchange catheter having a distal guidewire channel and a proximal guidewire channel. The catheter is exchanged by withdrawing the catheter from a guiding catheter until the guidewire can be removed from the proximal guidewire channel and then further withdrawn in the conventional fashion. The proximal guidewire channel provides a sealing surface for a releasable seal on the guiding catheter, avoiding the gripping of the guidewire.

14 Claims, 3 Drawing Sheets

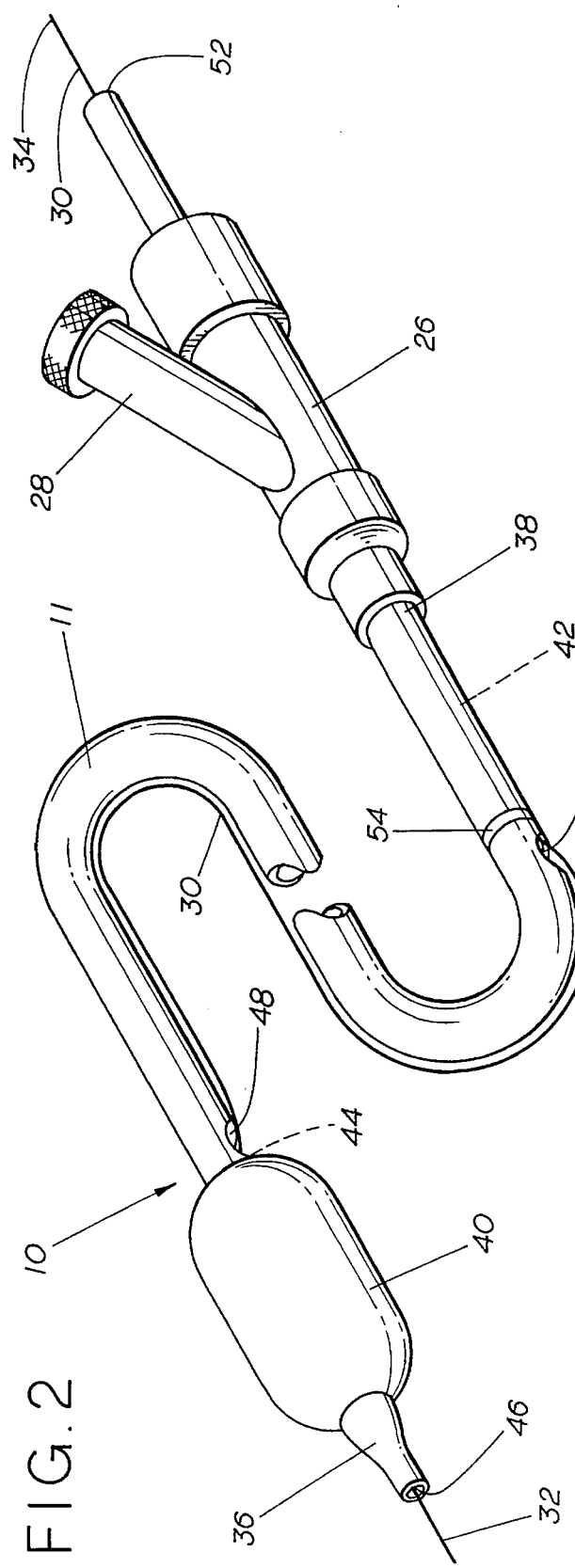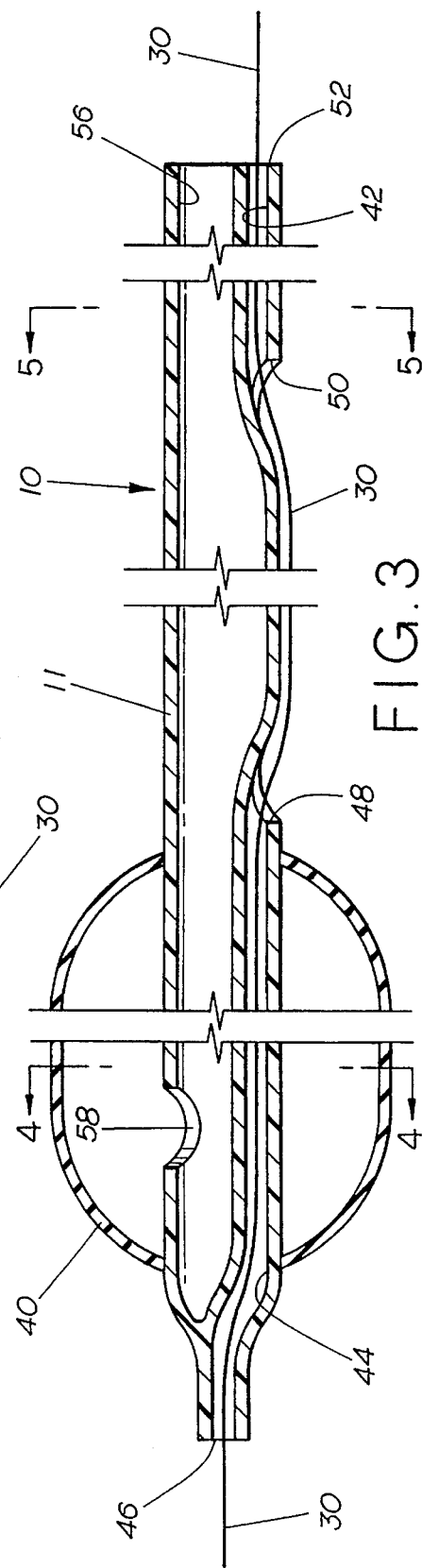

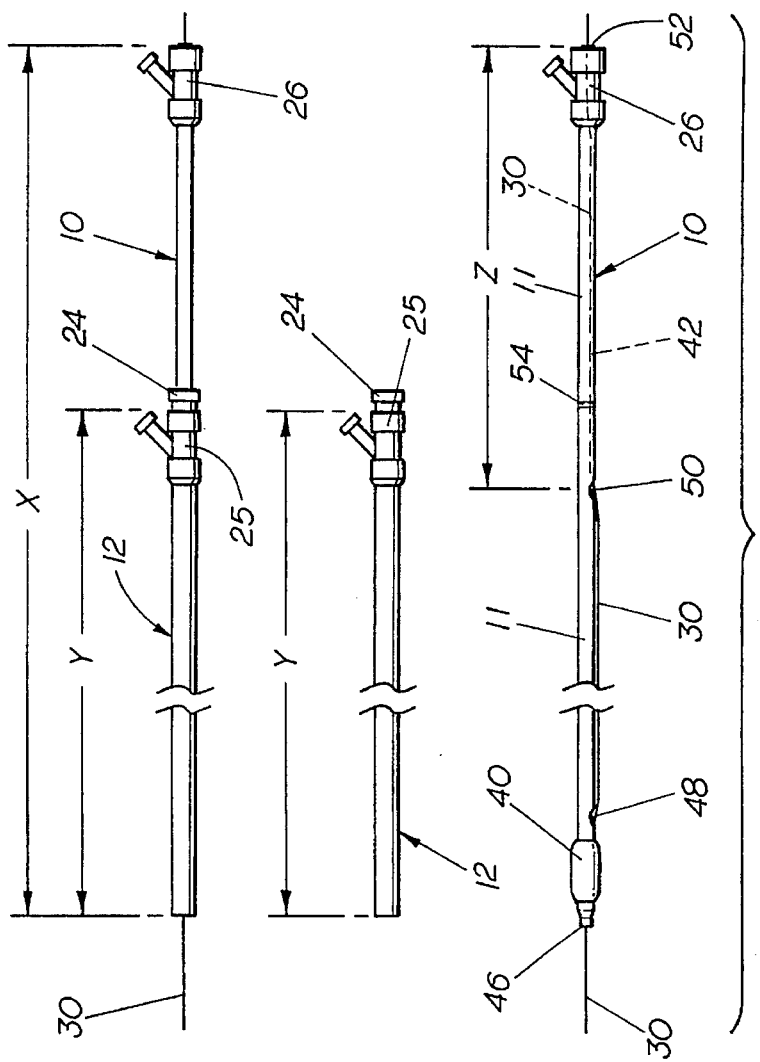
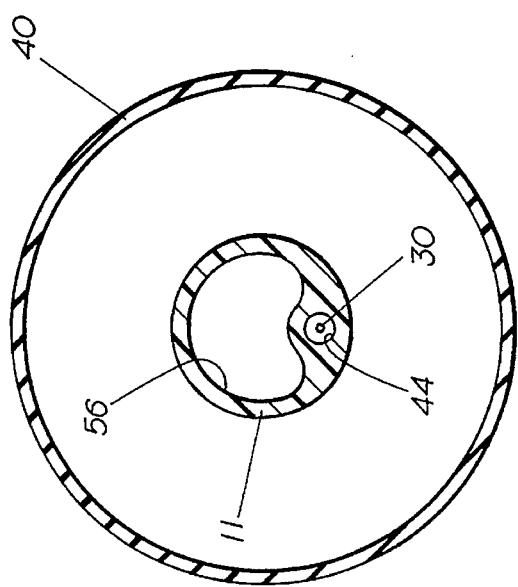
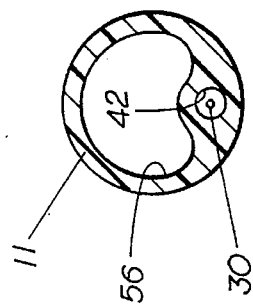

RAPID EXCHANGE CATHETER

RELATED APPLICATION

This application is a continuation of U.S. Patent application Ser. No. 092,332, filed Jul. 15, 1993.

FIELD OF INVENTION

The present invention is in the field of catheters which are inserted into body passageways of patients for various diagnostic and therapeutic treatment. Specifically, this invention pertains to a diagnostic or therapeutic catheter which can be inserted into a guiding catheter over a guidewire, followed by removal and replacement of the diagnostic or therapeutic catheter, over the same guidewire. Such catheters are commonly referred to as over-the-wire rapid-exchange (OTW-RE) catheters.

BACKGROUND OF THE INVENTION

Over-the-wire rapid-exchange catheters are adaptable for various applications involving various body passageways or cavities, one of which is an intravascular procedure called percutaneous transluminal coronary angioplasty (PTCA) for dilatation of a coronary stenosis. During the performance of the PTCA procedure, it is often necessary to remove the operative catheter, whether diagnostic or therapeutic in nature, and replace it with another operative catheter.

In the performance of a typical PTCA procedure, a guiding catheter is percutaneously introduced into the cardiovascular system of the patient. This guiding catheter typically has a distal tip which is shaped to enhance its ability to be advanced to the vicinity of the selected treatment area. The guiding catheter can be twisted or rotated to orient the shaped distal tip to follow the vascular passageways as desired. The distal tip of the guiding catheter is advanced through the cardiovascular system to the aorta, near the ostium, or mouth, of the coronary artery to be inspected or treated. At this point, the shaped distal tip of the guiding catheter is oriented into the coronary ostium.

An operative catheter is then inserted into the guiding catheter and advanced to the treatment area. The guiding catheter will typically incorporate a releasable seal near its proximal end, to seal the guiding catheter around the operative catheter and prevent back leakage of contrast dye or other fluids. The seal is typically an O-ring which can have its internal opening tightened around the operative catheter. The tightness of the seal is selectively adjusted by the physician during the procedure as required to allow movement of the catheter or guidewire, and to maintain a fluid tight seal. The operative catheter can have various operative means on its distal end, for diagnostic or therapeutic purposes. Other procedures could utilize a laser source or an image guide, or other means as required, but in the case of the PTCA procedure, the operative means is an inflatable angioplasty balloon. In the typical over-the-wire procedure, the operative catheter has a guidewire running through an inner guidewire channel in the catheter body. This guidewire channel is usually separate from the operative or communicative channel which operates the operative means, such as by inflating the angioplasty balloon in the PTCA procedure.

The guidewire runs from the proximal end of the operative catheter, through the guidewire channel, and out the distal end of the catheter body. The distal tip of the guidewire is normally shaped to facilitate its advancement into the coronary artery to be treated. The distal tip of the guidewire is advanced out the distal end of the operative catheter, past the ostium of the coronary artery, along the selected coronary artery to the treatment point. The guidewire can be twisted or rotated as required to orient the shaped distal tip of the guidewire to facilitate passage through the artery. The operative catheter can be sequentially moved along with the guidewire, or the guidewire can be advanced alone, to be followed by the operative catheter. Many physicians prefer to sequentially advance the operative catheter to assist in guiding the guidewire tip. For example, when two or more curves in the vascular passageway are encountered, it is often helpful to advance the guidewire through the first curve and then bring the operative catheter over the guidewire into the first curve. Then, the guidewire is advanced through the second curve, assisted by the support of the operative catheter. This calls for smooth movement of the operative catheter and guidewire, without interference from any unnecessary drag from the releasable seal, to allow the physician to feel the progress of the guidewire and catheter.

Eventually, in the PTCA procedure, the distal tip of the guidewire is advanced through the stenosis in the coronary artery. The operative dilatation catheter is then advanced over the guidewire until the balloon on the distal end of the operative catheter is positioned across the stenosis. The balloon is then inflated to dilate the stenosed area of the artery, deflated, and withdrawn to allow the resumption of blood flow. It is often necessary to withdraw the operative catheter and replace it with a second operative catheter to perform a different procedure, or to more effectively perform the procedure at hand. An example of the need for such an exchange can be to replace the balloon with a balloon of a different size.

Catheters have been devised which will allow the removal of the first operative catheter while holding the guidewire in place, followed by the insertion of a second operative catheter over the original guidewire. During this procedure, called a rapid exchange, it is still necessary to feel the advance of the operative catheter through the vascular passageways. It is also necessary to hold the guidewire in place, to avoid the time and risk involved in inserting a second guidewire, and to prevent the guidewire from partially withdrawing with the catheter. Most rapid exchange catheters have simply used a guidewire channel located near the distal end of the catheter body, through which the guidewire is threaded. From this distal guidewire channel, the guidewire typically simply passes alongside the catheter body to the proximal end of the catheter. This allows the physician to hold the guidewire in place while withdrawing the operative catheter until the distal guidewire channel has exited the guiding catheter. The physician can then grasp the guidewire distally from the distal end of the operative catheter and fully withdraw the operative catheter over the proximal end of the guidewire. The proximal end of the guidewire is then inserted through the distal guidewire channel on the replacement operative catheter, and the catheter is inserted to the treatment area over the guidewire.

The principal problem with such rapid exchange catheters is that the guidewire passes alongside the catheter body over most of its length. This means that the releasable seal in the guiding catheter must seal against the guidewire by pressing the guidewire against the outer surface of the operative catheter. This can require a tighter pressure by the sealing O-ring than would be required if the O-ring were in full contact with the outer wall of the catheter around its circumference. This creates a significant drag on the guidewire, which interferes with the physician's tactile feedback during initial insertion of the guidewire from the coronary ostium to the stenosis, and it can even increase the drag on the operative catheter during insertion over the guidewire. Both of these conditions are undesirable, especially at this particular juncture in the PTCA procedure, when the physician particularly needs the maximum possible tactile feedback.

In addition, it is difficult to coordinate the advancement of the catheter and separate guidewire through the guiding catheter. Finally, when the releasable seal is tightened against the catheter and guidewire, such as during dye injection, the guidewire exits the guiding catheter at an extreme angle relative to the operative catheter, which feels awkward to the physician.

Therefore, it is an object of the present invention to provide an over-the-wire rapid-exchange catheter which will allow the physician increased tactile feedback during advancement of the guidewire from the distal mouth of the guiding catheter through the stenosis and during advancement of the operative catheter over the guidewire. It is a further object of the present invention to provide an over-the-wire rapid-exchange catheter in which the guidewire does not contact the releasable seal in the guiding catheter, during advancement of the guidewire distal tip out of the distal end of the guiding catheter, and which presents a smooth sealing surface to the releasable seal.

SUMMARY OF THE INVENTION

The present invention provides an over-the-wire rapid-exchange catheter which has two integral guidewire channels, one near the distal end of the catheter body, and one near the proximal end of the catheter body. Each guidewire channel is a lumen passing longitudinally through the catheter body, sized to allow the free passage of a guidewire. Each guidewire channel has two ports through which the guidewire enters and exits the respective guidewire channel. The passage of the guidewire through the guidewire channels will be described by the use of the terms "enter" and "exit" as they would apply during threading of the proximal end of the guidewire through the guidewire channels from the distal end of the catheter body to the proximal end of the catheter body.

The operative catheter of the present invention has a flexible elongated catheter body. It is to be understood that the principles of the invention also could apply to a rigid catheter using an internal guide means or to a catheter of any length. A distal guidewire channel is formed into the catheter body near the distal end of the catheter body, running along the catheter body for a selected distance. The distal end of the distal guidewire channel contains a guidewire entry port which is located at the extreme distal tip of the operative catheter. The proximal end of the distal guidewire channel contains a guidewire exit port through which the guidewire exits the distal guidewire channel.

After exiting the distal guidewire channel, the guidewire passes alongside the catheter body through most of its length, until it approaches the proximal guidewire channel formed into the catheter body near its proximal end. The proximal guidewire channel has a re-entry port formed in its distal end, into which the guidewire passes to re-enter the catheter body. Finally, the guidewire exits the catheter body near the proximal end thereof, through a second exit port at the proximal end of the proximal guidewire channel.

The placement and length of the distal guidewire channel are designed as well known in the art according to the type of operative means mounted on the distal end of the operative catheter. Where the operative means is an angioplasty balloon, the distal guidewire channel passes through the distal end of the balloon, and the exit port of the distal guidewire channel is located proximally from the proximal end of the balloon. This allows the catheter to be withdrawn over the in-place guidewire until the balloon exits the guiding catheter, followed by grasping of the guidewire distally from the balloon to allow complete removal of the catheter from the guidewire.

The placement and length of the proximal guidewire channel, and consequently the placement of the distal and proximal ports of this channel, are designed to ensure that the releasable seal is situated around the proximal guidewire channel during the time when the guidewire and operative catheter are being advanced out of the distal end of the guiding catheter into the stenosed region of the artery. As explained earlier, the guiding catheter is inserted until its distal end is at the ostium of the artery. Subsequently, the operative catheter and its threaded guidewire are advanced through the guiding catheter until the distal end of the operative catheter is just short of the distal end of the guiding catheter. A reference mark on the catheter body aligns with the proximal end of the guiding catheter to demonstrate when the operative catheter has been inserted to this depth. This reference mark is on the portion of the catheter body which incorporates the proximal guidewire channel, so that the guidewire does not contact the releasable seal at the proximal end of the guiding catheter. In other words, the distal or re-entry port in the proximal guidewire channel is longitudinally located distally from the reference mark, and the proximal port in the proximal guidewire channel is longitudinally located proximally from the reference mark.

This placement of the distal and proximal ports of the proximal guidewire channel ensures that, once the operative catheter has been inserted nearly to the distal end of the guiding catheter at the ostium of the artery, the further sequential advancement of the guidewire and the operative catheter to penetrate and dilate the stenosis will take place without the releasable seal contacting the guidewire. Therefore, less pressure on the seal will be required, and increased tactile feedback will be provided to the physician. In addition, the guidewire will exit the catheter body essentially parallel to the catheter body, rather than at an awkward angle. Finally, the tightness of the releasable seal can be set, and advancement of the guidewire can take place without further adjustment.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 2 is a perspective view of the operative catheter shown in FIG. 1, with a guidewire installed;

FIG. 3 is a longitudinal sectional view of the operative catheter shown in FIG. 1;

FIG. 4 is a transverse sectional view of the operative catheter shown in FIG. 3, taken at line 4–4;

FIG. 5 is a transverse sectional view of the operative catheter shown in FIG. 3, taken at line 5–5; and FIG. 6 is a perspective view of the operative catheter of the present invention, and a typical guiding catheter, showing the relative longitudinal placement of the proximal guidewire channel.

DESCRIPTION OF PREFERRED EMBODIMENTS

Figure 1:
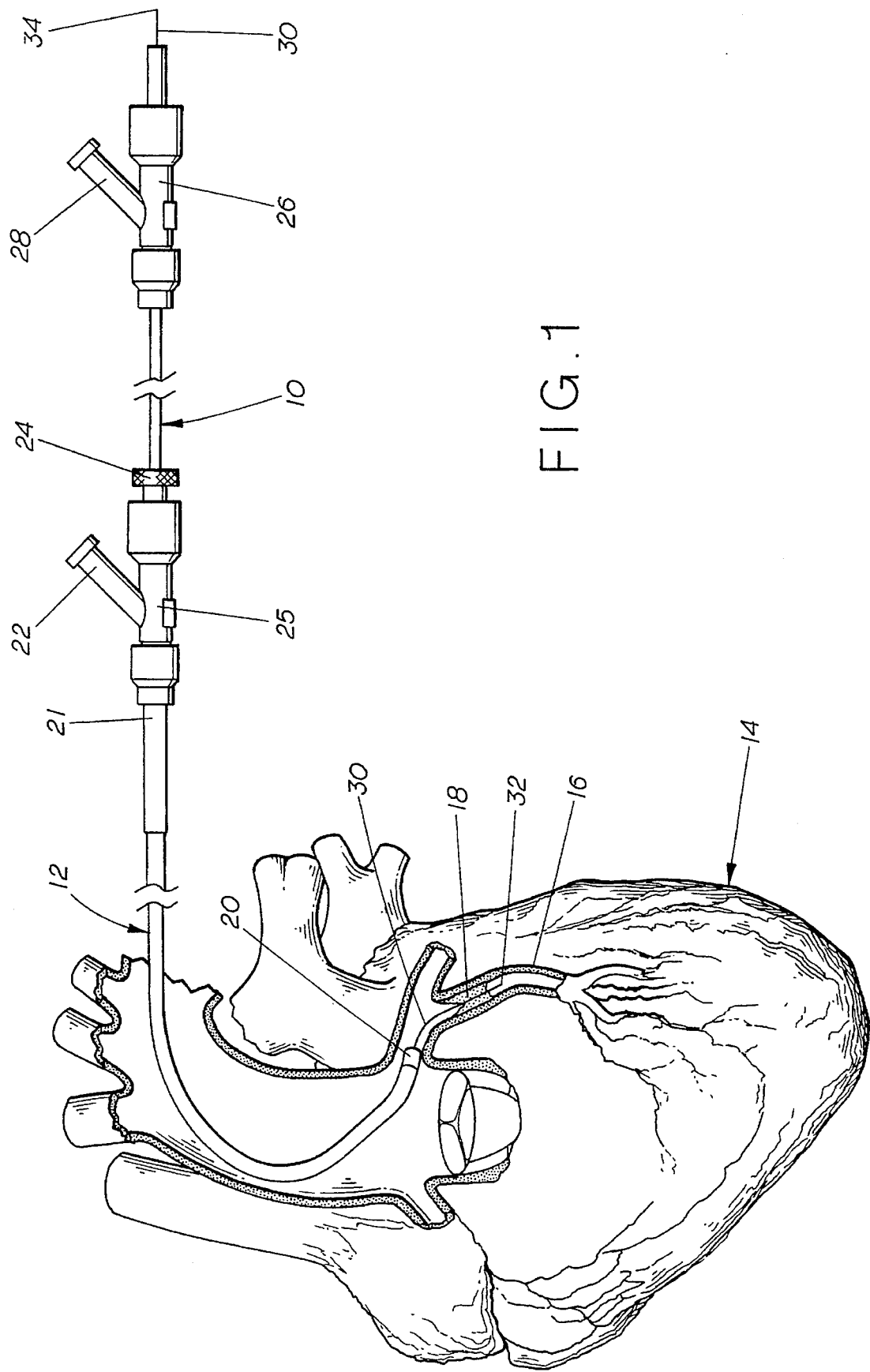
FIG. 1 is a schematic view of the operative catheter of the present invention in use.

As seen in FIG. 1, when in use, the operative catheter 10 is inserted through guiding catheter 12, which has been inserted, through the arteries, to the heart 14 of a patient. Heart 14 has a coronary artery 16 which is partially or completely occluded by stenosis 18. Distal end 20 of guiding catheter 12 has been positioned at the ostium of coronary artery 16, and guidewire 30 has been advanced toward stenosis 18. Distal end 32 of guidewire 30 is shown as having passed through stenosis 18 prior to advancement of operative catheter 10 out of guiding catheter 12, but in many situations, operative catheter 10 would be sequentially advanced with guidewire 30.

Proximal end 21 of guiding catheter 12 is joined to an adaptor 25 which contains releasable seal 24. Releasable seal 24 typically contains an O-ring which can be tightened to seal its internal opening around operative catheter 10 by tightening a nut. Contrast dye injection port 22 projects at an angle from adaptor 25. Adaptor 25 functions essentially as the proximal terminal of guiding catheter 12, and the proximal end of adaptor 25 will be considered, for the purposes of this discussion, to be the proximal end of guiding catheter 12. Guiding catheter 12, adaptor 25, and releasable seal 24 are items well known in the art. In FIG. 1, operative catheter 10 has been inserted into guiding catheter 12, through adaptor 25, until the distal end of operative catheter 10 is near, but just short of distal end 20 of guiding catheter 12.

A length of operative catheter 10 extends proximally from the proximal end of guiding catheter 12, with adaptor 26 attached thereto. Adaptor 26 is similar to adaptor 25 in that proximal end 34 of guidewire 30 extends therethrough, and inflation port 28 projects at an angle from adaptor 26. Inflation fluid is injected into inflation port 28 to inflate an angioplasty balloon on the distal end of operative catheter 10. Adaptor 26 functions essentially as the proximal terminal of operative catheter 10, and the proximal end of adaptor 26 will be considered, for the purposes of this discussion, to be the proximal end of operative catheter 10. Adaptor 26 is an item well known in the art.

As seen in FIG. 2, operative catheter 10 includes flexible elongated catheter body 11 having distal end 36 and proximal end 38. Angioplasty balloon 40 is mounted adjacent to distal end 36. Two hollow guidewire channels 42, 44 are formed into catheter body 11 at the proximal and distal ends thereof, respectively. Distal guidewire channel 44 has a distal guidewire entry port 46 at its extreme distal end and a first guidewire exit port 48 at its proximal end. Proximal guidewire channel 42 has guidewire re-entry port 50 at its distal end and a second guidewire exit port 52 at its proximal end, in this case at the proximal end of adaptor 26. Reference mark 54 is placed on catheter body 11, around proximal guidewire channel 42, between re-entry port 50 and final exit port 52.

FIG. 3 shows more detail of the functional construction of catheter body 11. Balloon 40 is mounted to catheter body 11 surrounding distal guidewire channel 44. Guidewire 30 exits port 48 and passes alongside catheter body 11, then re-enters at re-entry port 50. Guidewire 30 then finally exits catheter body 11 at exit port 52, schematically shown in this view as simply a port in the proximal end of catheter body 11. Balloon 40 is inflated via inflation channel 56 and balloon port 58. Inflation channel 56 is parallel to but isolated from guidewire channels 42, 44. FIG. 4 shows distal guidewire channel 44 in relation to inflation channel 56 and balloon 40. FIG. 5 shows proximal guidewire channel 42 in relation to inflation channel 56. Guidewire channels 42, 44 are shown as being formed along the edge of catheter body 11, next to inflation channel 56, but guidewire channels 42, 44 could be formed substantially coaxially with inflation channel 56, without departing from the spirit of the invention.

FIG. 6 shows a comparison between the lengths of operative catheter 10 and guiding catheter 12, and the relative longitudinal placement of the distal and proximal ports 50, 52 of proximal guidewire channel 42. Operative catheter 10 has a length X, while guiding catheter 12 has an appreciably shorter length Y. The distance Z between proximal exit port 52 and re-entry port 50 is greater than the difference between length X and length Y. Said another way, the distance (X minus Z) between the distal end 36 of operative catheter 10 and re-entry port 50 is less than the length Y of guiding catheter 12. This placement of proximal guidewire channel 42 and its ports 50, 52 ensures that when the distal end of operative catheter 10 is inserted near, but just short of the distal end of guiding catheter 12, releasable seal 24 will seal around the outer surface of catheter body 11, rather than guidewire 30.

OPERATION

Guiding catheter 12 is inserted through vascular passageways to the ostium of coronary artery 16. Operative catheter 10, with guidewire 30 threaded therethrough, is inserted into guiding catheter 12 until reference mark 54 is at the proximal end of guiding catheter 12. This ensures that the distal end of operative catheter 10 is near, but just short of, the distal end of guiding catheter 12, and re-entry port 50 is located distally from seal 24. Seal 24 is tightened as required. Guidewire 30 and operative catheter 10 are sequentially advanced across stenosis 18.

When exchange of the operative catheter is required, operative catheter 10 is withdrawn until re-entry port 50 is located outside of guiding catheter 12. Guidewire 30 is pulled distally out of proximal guidewire channel 42. Guidewire 30 is held in place while operative catheter 10 is further withdrawn until distal entry port 46 exits the guiding catheter 12. Guidewire 30 is grasped distally of the operative catheter 10, and the catheter is completely removed from the proximal end of guidewire 30. A replacement operative catheter is threaded onto guidewire 30 and advanced to the stenosis, while original guidewire 30 is held in place.

While the particular Rapid Exchange Catheter as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

I claim:

1. An operative catheter, for use through a guiding catheter having a releasable seal, said operative catheter comprising:

an elongated catheter body having a distal end and a proximal end;

an operative means mountable on said catheter body adjacent said distal end of said catheter body, for performing a diagnostic or therapeutic operation on a patient;

a communicative means extending through said catheter body from said proximal end of said catheter body to said operative means;

a distal guidewire channel formed on said catheter body adjacent said distal end of said catheter body, said distal guidewire channel terminating at a first distal port and a first proximal port; and a proximal guidewire channel separate from and substantially axially aligned with said distal guidewire channel, said proximal guidewire channel being formed on said catheter body adjacent said proximal end of said catheter body, said proximal guidewire channel terminating at a second distal port and a second proximal port;

wherein said second distal port and said second proximal port are longitudinally positioned along said catheter body so that installation of said operative catheter within the guiding catheter, with said operative means adjacent a distal end of the guiding catheter, locates the releasable seal on the guiding catheter between said second distal port and said second proximal port.

2. An operative catheter as claimed in claim 1, further comprising a reference mark placed on said catheter body between said second distal port and said second proximal port, said reference mark being placed at a longitudinal distance from said distal end of said catheter body, said longitudinal distance being slightly less than the length of the guiding catheter.

3. An operative catheter as claimed in claim 1, wherein said operative means comprises an angioplasty balloon.

4. An operative catheter as claimed in claim 3, wherein said communicative means comprises a fluid passageway extending longitudinally through said catheter body from said proximal end of said catheter body to said balloon.

5. An operative catheter as claimed in claim 4, wherein:

said distal guidewire channel is formed with, but isolated from, said fluid passageway;

said first distal port is longitudinally positioned distally from said balloon; and said first proximal port is longitudinally positioned proximally from said balloon.

6. An operative catheter as claimed in claim 5, wherein:

said proximal guidewire channel is formed with, but isolated from, said fluid passageway;

said second proximal port is longitudinally positioned at said proximal end of said catheter body; and said second distal port is longitudinally positioned distally from said second proximal port by a distance greater than the difference between the length of said catheter body and the length of the guiding catheter.

7. A vascular catheter system, comprising:

an elongated guiding catheter having a distal end and a proximal end;

a releasable seal mountable on said guiding catheter adjacent said proximal end of said guiding catheter;

an elongated operative catheter body having a distal end and a proximal end;

an operative means mountable on said operative catheter body adjacent said distal end of said operative catheter body, for performing a diagnostic or therapeutic operation on a patient;

a communicative means extending through said operative catheter body from said proximal end of said operative catheter body to said operative means;

a distal guidewire channel formed on said operative catheter body adjacent said distal end of said operative catheter body, said distal guidewire channel terminating at a first distal port and a first proximal port;

a proximal guidewire channel separate from said distal guidewire channel, said proximal guidewire channel being formed on said operative catheter body adjacent said proximal end of said operative catheter body, said proximal guidewire channel terminating at a second distal port and a second proximal port; and a guidewire passing through said distal guidewire channel, alongside said operative catheter body, and through said proximal guidewire channel, with a distal end of said guidewire extending distally through said first distal port and a proximal end of said guidewire extending proximally through said second proximal port;

wherein said second distal port and said second proximal port are longitudinally positioned along said operative catheter body so that installation of said operative catheter body within said guiding catheter, with said operative means adjacent said distal end of said guiding catheter, locates said releasable seal between said second distal port and said second proximal port.

8. A vascular catheter system as claimed in claim 7, further comprising a reference mark placed on said operative catheter body between said second distal port and said second proximal port, said reference mark being placed at a longitudinal distance from said distal end of said operative catheter body, said longitudinal distance being slightly less than the length of said guiding catheter.

9. A vascular catheter system as claimed in claim 7, wherein said operative means comprises an angioplasty balloon.

10. A vascular catheter system as claimed in claim 9, wherein said communicative means comprises a fluid passageway extending longitudinally through said operative catheter body from said proximal end of said operative catheter body to said balloon.

11. A vascular catheter system as claimed in claim 10, wherein:

said distal guidewire channel is formed with, but isolated from, said fluid passageway;

said first distal port is longitudinally positioned distally from said balloon; and said first proximal port is longitudinally positioned proximally from said balloon.

12. A vascular catheter system as claimed in claim 11, wherein:

said proximal guidewire channel is formed with, but isolated from, said fluid passageway;

said second proximal port is longitudinally positioned at said proximal end of said operative catheter body; and said second distal port is longitudinally positioned distally from said second proximal port by a distance greater than the difference between the length of said operative catheter body and the length of said guiding catheter.

13. A method of removing a first over-the-wire operative catheter from a guiding catheter in a patient, and replacing it with a second operative catheter, over the same wire, the method comprising the steps of:

withdrawing said first operative catheter from said guiding catheter, while holding said guidewire in place by its proximal end, until a guidewire channel on the proximal end of said first operative catheter exits said guiding catheter;

removing said proximal end of said guidewire from said proximal guidewire channel;

further withdrawing said first operative catheter from said guiding catheter, while holding said guidewire in place by its proximal end, until a guidewire channel on the distal end of said first operative catheter exits said guiding catheter;

removing said guidewire from said distal guidewire channel;

threading said proximal end of said guidewire through a distal guidewire channel on a second operative catheter; and inserting said second operative catheter into said guiding catheter over said guidewire.

14. A method of rapid replacement of a first operative catheter with a second operative catheter, the method comprising the steps of:

providing a guiding catheter having a releasable seal;

inserting said guiding catheter through an internal passageway of a patient to a selected treatment area;

providing a first operative catheter having a distal guidewire channel and a proximal guidewire channel;

providing a guidewire;

positioning said guidewire alongside said first operative catheter, said guidewire passing through said distal guidewire channel and through said proximal guidewire channel;

inserting said first operative catheter and said guidewire through said guiding catheter to a depth at which said releasable seal surrounds said proximal guidewire channel;

selectively sealingly engaging said releasable seal with said first operative catheter;

withdrawing said first operative catheter from said guiding catheter, while holding said guidewire in place by its proximal end, until said proximal guidewire channel exits said guiding catheter;

removing said proximal end of said guidewire from said proximal guidewire channel;

further withdrawing said first operative catheter from said guiding catheter, while holding said guidewire in place by its proximal end, until said distal guidewire channel exits said guiding catheter;

removing said guidewire from said distal guidewire channel;

providing a second operative catheter having a distal guidewire channel;

threading said proximal end of said guidewire through said distal guidewire channel on said second operative catheter; and inserting said second operative catheter into said guiding catheter over said guidewire.

* * * * *